US006946141B2

(12) United States Patent
Tam et al.

(10) Patent No.: US 6,946,141 B2
(45) Date of Patent: Sep. 20, 2005

(54) AS-NEEDED ADMINISTRATION OF TRICYCLIC AND OTHER NON-SRI ANTIDEPRESSANT DRUGS TO TREAT PREMATURE EJACULATION

(75) Inventors: Peter Tam, Redwood City, CA (US); Neil Gesundheit, Los Altos, CA (US); Leland F. Wilson, Menlo Park, CA (US)

(73) Assignee: Vivus, Inc., Mountain View, CA (US)

( * ) Notice: Subject to any disclaimer, the term of this patent is extended or adjusted under 35 U.S.C. 154(b) by 92 days.

(21) Appl. No.: 09/996,407

(22) Filed: Nov. 21, 2001

(65) Prior Publication Data

US 2002/0161016 A1 Oct. 31, 2002

Related U.S. Application Data

(63) Continuation-in-part of application No. 09/721,412, filed on Nov. 21, 2000, now Pat. No. 6,495,154.

(51) Int. Cl.$^7$ ............................. A61F 2/02; A61F 13/02; A61K 9/48; A61K 9/70; A61K 9/04

(52) U.S. Cl. ....................... 424/423; 424/434; 424/435; 424/443; 424/449; 424/451; 424/464; 424/45; 424/46

(58) Field of Search ................................ 424/423, 434, 424/435, 443, 449, 451, 464, 45, 46

(56) References Cited

U.S. PATENT DOCUMENTS

| | | | |
|---|---|---|---|
| 3,467,650 A | | 9/1969 | Schindler et al. |
| 3,665,073 A | | 5/1972 | Marshall et al. |
| 4,507,323 A | | 3/1985 | Stern |
| 4,940,731 A | | 7/1990 | Bick |
| 5,151,448 A | * | 9/1992 | Crenshaw et al. .......... 514/651 |
| 5,276,042 A | * | 1/1994 | Crenshaw et al. .......... 514/321 |
| 5,707,999 A | * | 1/1998 | Cavallini ............... 514/252.17 |
| 5,830,500 A | * | 11/1998 | El-Rashidy et al. ........ 424/465 |
| 5,922,341 A | * | 7/1999 | Smith et al. ................. 424/430 |
| 6,096,738 A | | 8/2000 | Bernstein |

FOREIGN PATENT DOCUMENTS

| | | |
|---|---|---|
| BR | PI 9806330-8 A | 9/2000 |
| EP | 0415613 | * 3/1991 |
| WO | WO 98/43646 | 10/1998 |
| WO | WO 99/21508 | 5/1999 |

OTHER PUBLICATIONS

Abdel–Hamid et al. (Feb. 2001), "Assessment of as Needed Use of Pharmacotherapy and the Pause–Squeeze Technique in Premature Ejaculation," *International Journal of Impotence Research* 13(1):41–45.
Althof et al. (1995), "A Double–Blind Crossover Trial of Clomipramine for Rapid Ejaculation in 15 Couples," *J. Clin. Psychiatry* 56(9):402–407.
Althof et al. (1995), "Early Experience with Clomipramine for Rapid Ejaculation," *Proceedings of the American Urological Association* 153:474A.
Assalian (1988), "Clomipramine in the Treatment of Premature Ejaculation," *The Journal of Sex Research* 24:213–215.
Balon (1996), "Antidepressant in the Treatment of Premature Ejaculation," *Journal of Sex and Marital Therapy* 22(2):85–96.
Girgis et al. (1982), "A Double–Blind Trial of Clomipramine in Premature Ejaculation," *Andrologia* 14(4):364–368.
Goodman (1977), "The Management of Premature Ejaculation," *J. Int. Med. Res.* 5(Supplement 1):78–79.
Haensel et al. (1996), "Clomipramine and Sexual Function in Men with Premature Ejaculation and Controls," *The Journal of Urology* 156:1310–1315.
Kim et al. (1998), "Treatment of Premature Ejaculation," *The Journal of Family Practice* 46(4):280–281.
Kim et al. (1998), "Efficacy and Safety of Fluoxetine, Sertraline and Clomipramine in Patients with Premature Ejaculation: A Double–Blind, Placebo Controlled Study," *The Journal of Urology* 159:425–427.
Kolomaznik et al. (1999), "Přdčsná Ejakulace" ("Premature Ejaculation"), *C.S. Psychiat.* 95(8):516–523 (English translation included).
Rowland et al. (1998), "The Treatment of Premature Ejaculation: Psychological and Biological Strategies," *Drugs of today* 34(10):879–899.
Segraves et al. (1993), "Clomipramine versus Placebo in the Treatment of Premature Ejaculation: A Pilot Study," *Journal of Sex & Marital Therapy* 19(3):198–200.
Strassberg et al. (1999), "Clomipramine in the Treatment of Rapid (Premature) Ejaculation," *Journal of Sex & Marital Therapy* 25(2):89–101.
Hsieh et al. (1988), "In Vivo Evaluation of Serotonergic Agent and α–Adrenergic Blockers on Premature Ejaculation by Inhibiting the Seminal Vesicle Pressure Response to Electrical Nerve Stimulation," *British Journal of Urology* 82:237–240.
Rothschild (2000), "New Directions in the Treatment of Antidepressant–Induced Sexual Dysfunction," *Clinical Therapeutics* 22(Suppl. A):A42–A61.
Beers and Berkow, Editors, *The Merk Manual of Diagnosis and Therapy*, 17$^{th}$ Edition, pp. 1558–1559, Merk Research Laboratories, Whitehouse Station, NJ, USA.
Kulik et al. (1982), "Case Report of Painful Ejaculation of a Side Effect of Amoxipine," *Am. J. Psychiatry* 139(2):234–235.

* cited by examiner

*Primary Examiner*—Carlos Azpuru
(74) *Attorney, Agent, or Firm*—Dianne E. Reed; Reed Intellectual Property Law Group

(57) ABSTRACT

A method is provided for treatment of premature ejaculation by administration of an antidepressant drug selected from tricyclic antidepressants, tetracyclic antidepressants, MAO inhibitors, azaspirone antidepressants, and atypical non-SRI antidepressants. In a preferred embodiment, administration is on as "as-needed" basis, i.e., the drug is administered immediately or at most several hours prior to sexual activity. Pharmaceutical formulations and packaged kits are also provided.

68 Claims, No Drawings

AS-NEEDED ADMINISTRATION OF TRICYCLIC AND OTHER NON-SRI ANTIDEPRESSANT DRUGS TO TREAT PREMATURE EJACULATION

CROSS-REFERENCE TO RELATED APPLICATIONS

This application is a continuation-in-part of U.S. patent application Ser. No. 09/721,412, filed Nov. 21, 2001, now U.S. Pat. No. 6,495,154, the disclosure of which is hereby incorporated by reference.

TECHNICAL FIELD

This invention relates generally to methods and pharmaceutical compositions for the treatment of premature ejaculation. More particularly, the invention relates to the use of tricyclic, tetracyclic, and other antidepressant drugs in such methods and compositions.

BACKGROUND

Premature ejaculation is a debilitating yet common sexual dysfunction, and has been estimated to affect at least 30 to 40 percent of men at some point in their lives (Derogatis (1980) *Med. Aspects Hum. Sexuality* 14:1168–76; Frank et al. (1978) *New Engl. J. Med.* 299:111–115; Schein et al. (1988) *Fam. Pract. Res. J.* 7(3):122–134). The condition can lead to an inability to enter into or sustain relationships, can cause psychological damage to sufferers, and can also impair reproductive success.

The Diagnostics and Statistical Manual of Mental Disorders (DSM-IV) (Washington, D.C.: American Psychiatric Association, 1994) delineates three criteria for a diagnosis of premature ejaculation: (1) "persistent or recurrent ejaculation with minimal sexual stimulation before, on or shortly after penetration and before the person wishes it," which is (2) associated with "marked distress or interpersonal difficulty," and (3) not due exclusively to the "direct" effects of a "substance" (with withdrawal from opioids cited as an example). The disorder is usually primary, but can also be secondary. "Primary" premature ejaculation refers to a lifelong, typically congenital condition, while "secondary" premature ejaculation refers to a late onset condition, acquired after a period of normal functioning. Sexual dysfunctions such as premature ejaculation may also be further characterized as being generalized or limited to certain situations, and with respect to degree or frequency of the disturbance.

Premature ejaculation has historically been treated by psychosexual counseling in combination with "behavioral" therapies such as the so-called "pause" and "pause-squeeze" techniques. See St. Lawrence et al. (1992), "Evaluation and Treatment of Premature Ejaculation: A Critical Review," *Int. J. Psychiatry in Medicine* 22(1):77–97; Semans, "Premature Ejaculation: A New Approach," *Southern Medical Journal* 49:353–357, regarding the "pause" technique; and Masters and Johnson, *Human Sexual Inadequacy*, Little, Brown & Company, Boston, Mass., 1970, regarding the "pause-squeeze" technique. Any improvement resulting from the aforementioned techniques is short-lived, however, and the cooperation of a man's sexual partner is required. Typically, psychosexual counseling also requires the cooperation of the partner. Furthermore, many men may demand a quicker solution to the problem or are unwilling to attend counseling sessions. In addition, psychosexual counseling requires specialized therapists who may not be available to all patients, particularly in remote locations. Finally, counseling benefits only a subset of patients, i.e., those for whom the condition is psychogenic. Psychological therapies cannot alleviate premature ejaculation resulting from non-psychological causes.

Topical anesthetic agents and intracavernosal injection of medicaments have also been employed to treat patients suffering from premature ejaculation. However, anesthetic agents are problematic insofar as they necessarily decrease tissue sensitivity and thereby diminish sexual pleasure. Also, topical anesthetics can be transferred to sexual partners and thereby decrease their sensitivity and pleasure as well. Intracavernosal injection is associated with pain and discomfort, and is not a preferred mode of drug administration. Various devices have also been proposed to delay ejaculation; however, such devices can be awkward, inconvenient and embarrassing to use.

Methods for treating premature ejaculation by systemic administration of serotonin reuptake inhibitors (SRIs), including selective serotonin reuptake inhibitors (SSRIs), have been described (U.S. Pat. Nos. 4,507,323, 4,940,731, 5,151,448, and 5,276,042; PCT Publication No. W095/13072). For example, administration of the antidepressant fluoxetine (commercially available under the tradename Prozac® from Eli Lilly & Company), an SSRI, has been claimed to treat premature ejaculation; see U.S. Pat. No. 5,151,448. However, the administration of fluoxetine has many undesired aspects. Patients with hepatic or renal impairments may not be able to use fluoxetine due to its metabolism in the liver and excretion via the kidney. Systemic events during fluoxetine treatment involving the lungs, kidneys or liver have occurred, and death has occurred from overdoses. In addition, numerous side effects are associated with oral fluoxetine administration include hair loss, nausea, vomiting, dyspepsia, diarrhea, anorexia, anxiety, nervousness, insomnia, drowsiness, fatigue, headache, tremor, dizziness, convulsions, sweating, pruritis, and skin rashes. Fluoxetine interacts with a range of drugs, often by impairing their metabolism by the liver.

U.S. Pat. No. 4,940,731 describes the oral or parenteral administration of another SSRI, sertraline (commercially available under the tradename Zoloft® from Pfizer), for treating premature ejaculation. It has been recognized that sertraline shares many of the same problems as fluoxetine; see Martindale, *The Extra Pharmacopoeia*, 31st edition, at p. 333 (London: The Royal Pharmaceutical Society, 1996). Sertraline is metabolized in the liver, and is excreted in the urine and feces. Thus, patients with cirrhosis must take lower doses, and caution must be exercised when administering sertraline to patients with renal impairment. Individuals taking monoamine oxidase inhibitors cannot take sertraline due to the risk of toxicity. Side effects resulting from oral sertraline administration include nausea, diarrhea, dyspepsia, insomnia, somnolence, sweating, dry mouth, tremor and mania. Rare instances of coma, convulsions, fecal incontinence and gynecomastia have occurred in patients undergoing sertraline therapy.

U.S. Pat. No. 5,276,042 describes the administration of paroxetine (commercially available under the tradename Paxil® from SmithKline Beecham), an additional SSRI, for the treatment of premature ejaculation. Paroxetine is predominantly excreted in the urine, and decreased doses are recommended in patients with hepatic and renal impairments. Like sertraline, paroxetine cannot be given to patients undergoing treatment with a monoamine oxidase inhibitor. Side effects from oral administration of paroxetine include hyponatremia, asthenia, sweating, nausea, decreased appetite, oropharynx disorder, somnolence, dizziness, insomnia, tremor, anxiety, impaired micturition, weakness and paresthesia.

All of the known methods to treat premature ejaculation are thus problematic in one or more respects. An ideal method would not require ongoing ("chronic") drug therapy or use of active agents with numerous and/or serious side effects. An ideal method would be useful in the treatment of individuals with secondary, acquired premature ejaculation as well as those suffering from a primary, lifelong condition. The method would not involve application of anesthetic agents, intracavemosal drug administration, or use of devices, and would not require ongoing counseling sessions.

Thus there is a need for methods and dosage forms for treating premature ejaculation that requires no specialized psychological therapy, can be used conveniently and without embarrassment, and avoids the disadvantages associated with prior therapeutic methods and dosage forms.

Accordingly, the present invention is addressed to the limitations of the prior art, and provides a novel treatment for individuals suffering from either primary or secondary premature ejaculation, wherein drug administration may be on an "as-needed" basis rather than necessarily involving chronic pharmacotherapy, and does not involve use of anesthetic agents, intracavemosal drug administration, or use of devices. To the best of applicants' knowledge, the present method of treating premature ejaculation is novel and completely unsuggested by the prior art.

SUMMARY OF THE INVENTION

It is a primary object of the invention to address the above-described need in the art by providing a novel method for the treatment of premature ejaculation by administering an effective amount of an antidepressant drug selected from tricyclic, tetracyclic, and other non-SRI antidepressant agents to an individual in need of such therapy, on an "as-needed" basis. That is, the method does not involve chronic pharmacotherapy; rather, administration is on an "as-needed" basis, wherein "as-needed" administration involves administration shortly before anticipated sexual activity. The term "antidepressant agent" includes such agents per se as well pharmaceutically acceptable, pharmacologically active salts, esters, amides, prodrugs, active metabolites, conjugates, and other analogs thereof Administration of the drug may be carried out using any systemic mode of administration.

It is another object of the invention to provide such a method wherein the antidepressant drug is administered orally.

It is another object of the invention to provide such a method wherein the antidepressant drug is administered parenterally, transdermally, sublingually, buccally, nasally, transrectally, transurethrally, or via inhalation, or by other routes.

It is still another object of the invention to provide such a method wherein the antidepressant drug is a tricyclic antidepressant.

It is still another object of the invention to provide such a method wherein the antidepressant drug is a tetracyclic antidepressant.

It is still another object of the invention to provide such a method wherein the antidepressant drug is a monoamine oxidase inhibitor (MAOI).

It is still another object of the invention to provide such a method wherein the antidepressant drug is a non-SRI antidepressant drug not encompassed by the foregoing groups.

It is another object of the invention to provide a dosage form for delaying the onset of ejaculation in a male individual, comprising a rapid-release formulation for systemic absorption containing an active agent selected from the group consisting of tricyclic, tetracyclic, and other non-SRI antidepressants, in an amount effective to delay the onset of ejaculation by the individual during sexual activity.

Additional objects, advantages and novel features of the invention will be set forth in part in the description which follows, and in part will become apparent to those skilled in the art upon examination of the following, or may be learned by practice of the invention.

In a first aspect of the invention, a method is provided for the treatment of an individual prone to or suffering from premature ejaculation, the method comprising systemically administering to an individual in need of such treatment a therapeutically effective amount of an antidepressant drug selected from the group consisting of tricyclic antidepressants, tetracyclic antidepressants, azaspirone antidepressants, MAOIs, and other non-SRI antidepressants. In contrast to serotonin reuptake inhibitors such as paroxetine, sertraline, and fluoxetine, the present agents do not exhibit any significant side effects and do not require chronic administration for effectiveness. By contrast, administration of the active agents disclosed herein is an "as-needed" basis. By "as-needed" dosing, also known as pro re nata dosing, is meant the administration of a single dose of the active agent at some time prior to anticipated sexual activity. Administration can be immediately prior to sexual activity, or up to about 2 or 3 hours prior to anticipated sexual activity. Drug delivery may be accomplished through any mode of administration, including, but not limited to, the oral route.

In a further aspect of the invention, pharmaceutical formulations are provided for carrying out the method of the invention. The pharmaceutical formulations comprise a therapeutically effective amount of an active agent as provided herein, and a pharmacologically acceptable carrier or vehicle. Other types of components may be incorporated into the formulation as well, e.g., excipients, surfactants, preservatives (e.g., antioxidants), stabilizers, chelating agents, and the like, as will be appreciated by those skilled in the art of pharmaceutical formulation preparation and drug delivery. The pharmaceutical dosage form may be any dosage form suitable for systemic absorption and may be, but is not limited to, rapidly disintegrating tablets, effervescent tablets, sublingual tablets, buccal dosage forms, sublingual sprays, gum formulations or inhalers. Preferably, the dosage form is an immediate release oral formulation.

In another aspect of the invention, a packaged kit is provided for a patient to use in the treatment of premature ejaculation. The kit includes a pharmaceutical formulation of an antidepressant agent as provided herein, a container housing the pharmaceutical formulation during storage and prior to administration, and instructions, e.g., written instructions on a package insert or label, for carrying out drug administration in a manner effective to treat premature ejaculation. The pharmaceutical formulation may be any formulation described herein, e.g., an oral dosage form containing a unit dosage of the active agent, the unit dosage being a therapeutically effective dosage for treatment of premature ejaculation.

DETAILED DESCRIPTION OF THE INVENTION

I. Definitions and Overview

Before describing the present invention in detail, it is to be understood that this invention is not limited to specific active agents, dosage forms, dosing regimens, or the like, as such may vary. It is also to be understood that the terminology used herein is for the purpose of describing particular embodiments only, and is not intended to be limiting.

It must be noted that as used in this specification and the appended claims, the singular forms "a," "an" and "the" include plural referents unless the context clearly dictates otherwise. Thus, for example, reference to "an active agent" or "a pharmacologically active agent" includes a single active agent as well a mixture or combination of two or more different active agents, reference to "a carrier" includes mixtures of two or more carriers as well as a single carrier, and the like.

In describing and claiming the present invention, the following terminology will be used in accordance with the definitions set out below.

The terms "active agent," "pharmacologically active agent" and "drug" are used interchangeably herein to refer to a chemical compound that induces a desired pharmacological, physiological effect, i.e., in this case, treatment of premature ejaculation. The primary active agents herein are antidepressant agents that do not act as serotonin reuptake inhibitors, and are thus termed "non-SRI" antidepressants. The terms also encompass pharmaceutically acceptable, pharmacologically active derivatives of those active agents specifically mentioned herein, including, but not limited to, salts, esters, amides, prodrugs, active metabolites, conjugates, analogs, and the like. When the terms "active agent," "pharmacologically active agent" and "drug" are used, then, or when an active agent such as a tricyclic or tetracyclic antidepressant is specifically identified, it is to be understood that applicants intend to include the active agent per se as well as pharmaceutically acceptable, pharmacologically active salts, esters, amides, prodrugs, metabolites, conjugates, analogs, etc.

By "pharmaceutically acceptable," such as in the recitation of a "pharmaceutically acceptable carrier," or a "pharmaceutically acceptable acid addition salt," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active") as in a "pharmacologically active" derivative or metabolite, refers to a derivative or metabolite having the same type of pharmacological activity as the parent compound and approximately equivalent in degree. When the term "pharmaceutically acceptable" is used to refer to a derivative (e.g., a salt) of an active agent, it is to be understood that the compound is pharmacologically active as well, i.e., therapeutically effective in the treatment of premature ejaculation. "Carriers" or "vehicles" as used herein refer to conventional pharmaceutically acceptable carrier materials suitable for drug administration, and include any such materials known in the art that are nontoxic and do not interact with other components of a pharmaceutical composition or drug delivery system in a deleterious manner.

The terms "treating" and "treatment" as used herein refer to the ability to increase an individual's ejaculatory latency (i.e., delay ejaculation) during sexual activity, particularly sexual intercourse, relative to that individual's ejaculatory latency in the absence of pharmacotherapy as provided herein. Preferably, upon treatment according to the present invention, an individual's ejaculatory latency is increased by at least a factor of two, more preferably a factor of four and most preferably a factor of at least ten.

By an "effective" amount or a "therapeutically effective amount" of a drug or pharmacologically active agent is meant a nontoxic but sufficient amount of the drug or agent to provide the desired effect, i.e., of a drug or pharmacologically active agent is meant a nontoxic but sufficient amount of the drug or agent to provide the desired effect, i.e., an increase in ejaculatory latency as explained above. The amount that is "effective," however, will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation.

By "as-needed" dosing, also referred to as "pro re nata" dosing, "pm" dosing, and "on-demand" dosing or administration, is meant the administration of an active agent at a time just prior to the time at which drug efficacy is wanted, e.g., just prior to anticipated sexual activity, and within a time interval sufficient to provide for the desired therapeutic effect, i.e., enhancement in sexual desire and in sexual responsiveness during sexual activity. "As-needed" administration herein does not involve priming doses or chronic administration, "chronic" meaning administration at regular time intervals on an ongoing basis. As-needed administration may involve administration immediately prior to sexual activity, but will generally be about 0.25 to 3.5 hours, preferably about 0.5 to 3 hours, and most preferably about 1 to 2.5 hours prior to anticipated sexual activity. "As-needed" administration may or may not involve administration of a sustained release formulation in advance of anticipated sexual activity, with drug release taking place throughout an extended drug delivery period typically in the range of about 4 to 72 hours.

By the term "transdermal" drug delivery is meant delivery by passage of a drug through the skin or mucosal tissue and into the bloodstream. "Transdermal" delivery is also intended to encompass passage through scrotal skin.

By "transmucosal" drug delivery is meant administration of a drug to the mucosal surface of an individual so that the drug passes through the mucosal tissue and into the individual's blood stream. Transmucosal drug delivery may be "buccal" or "transbuccal," referring to delivery of a drug by passage through an individual's buccal mucosa and into the bloodstream. Another form of transmucosal drug delivery herein is "sublingual" drug delivery, which refers to delivery of a drug by passage of a drug through an individual's sublingual mucosa and into the bloodstream. An additional form of transmucosal drug delivery herein is "rectal" or "transrectal" drug delivery, referring to delivery of a drug by passage of a drug through an individual's rectal mucosa and into the bloodstream. Another form of transmucosal drug delivery is "urethral" or "transurethral" delivery, referring to delivery of the drug into the urethra such that the drug contacts and passes through the wall of the urethra.

"Rapidly disintegrating" as in a "rapidly disintegrating tablet" as used herein refers to a tablet that dissolves or disperses in manner that allows for the absorption of the active agent such that "as-needed" administration of the active agent is possible. Thus, many rapidly disintegrating tablets often, but not necessarily, include a disintegrant in the tablet formulation or are otherwise specially designed to quickly disintegrate upon administration.

In order to carry out the method of the invention, a selected non-SRI antidepressant drug is administered to a male individual suffering from or prone to premature ejaculation, either chronic, lifelong ("primary") premature ejaculation or acquired ("secondary") premature ejaculation. The active agent may be administered orally, transmucosally (including buccally, sublingually, transurethrally, and rectally), transdermally, by inhalation, or using any other route of administration. Oral administration, because of its convenience, is preferred for those active agents that have sufficient oral bioavailability.

II. Active Agents

The active agent administered using the method of the invention is a non-SRI antidepressant drug. The drug may be a tricyclic antidepressant, a tetracyclic antidepressant, an MAO inhibitor, an azaspirone antidepressant, or a non-SRI antidepressant not encompassed by the aforementioned groups. Any non-SRI antidepressant drug may be used so long as the drug is effective in delaying the onset of ejaculation.

Tricyclic antidepressants are conventionally identified by their characteristic "tricyclic," e.g., iminodibenzyl, dibenzyocycloheptadiene, and dibenzyloxepinylidene, cores. Tetracyclic antidepressants generally have a similar tricyclic core wherein two central carbons are connected through a lower alkylene bridge, thereby forming a fourth ring. Examples of tricyclic and tetracyclic antidepressants include, without limitation, amitryptiline, amoxapine, butriptyline, clomipramine, demexiptiline, desipramine, dibenzepin, dimetacrine, dothiepin, doxepin, imipramine, iprindole, lofepramine, maprotiline, melitracen, metapramine, mianserin, mirtazapine, nortryptiline, propizepine, protriptyline, quinupramine, setiptiline, tianeptine, trimipramine, and pharmacologically acceptable salts thereof. Clomipramine(3-chloro-10,11-dihydro-N,N-dimethyl-5H-dibenz[b,f]azepine-5-propanamine) and its pharmacologically acceptable acid addition salts thereof, e.g., clomipramine hydrochloride, are particularly preferred herein.

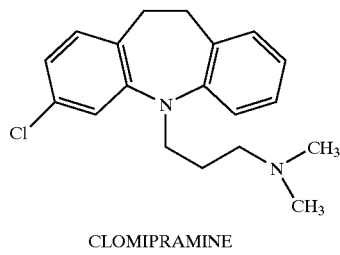

CLOMIPRAMINE

Monoamine oxidase inhibitors represent another class of antidepressant drugs suitable for use in accordance with the present invention. Representative monoamine oxidase inhibitors include amiflamine, brofaromine, clorgyline, α-ethyltryptamine, iproclozide, iproniazid, isocarboxazid, mebanazine, moclobemide, nialamide, pargyline, phenelzine, pheniprazine, pirlindole, safrazine, selegiline, toloxatone, tranylcypromine, and pharmacologically acceptable salts thereof.

Another class of suitable antidepressant drugs for use in conjunction with the present method are the azaspirones, including, without limitation, buspirone, gepirone, ipsapirone, tandospirone, tiaspirone, and pharmacologically acceptable salts thereof.

Other, "atypical," non-SRI antidepressants suitable for use herein include, by way of example, example, amesergide, amineptine, benactyzine, bupropion, fezolamine, levoprotiline, medifoxamine, mianserin, minaprine, oxaflozane, oxitriptan, rolipram, teniloxazine, tofenacin, trazadone, tryptophan, viloxazine, and pharmacologically acceptable salts thereof.

A single antidepressant agent may be administered, or a combination of antidepressants agents may be administered, in either a single formulation, or in separate formulations, and in the latter case, either simultaneously or sequentially. Additionally, one or more additional active agents can be administered with the antidepressant agent, either simultaneously or sequentially. The additional active agent will generally although not necessarily be one that is effective in treating premature ejaculation, and/or an agent that potentiates the effect of the antidepressant agent. Such agents include, for example, phosphodiesterase inhibitors, including Type III phosphodiesterase inhibitors (e.g., bipyridines such as milrinone, amrinone and olprinone; imidazolones such as piroximone and enoximone; imidazolines such as imazodan and 5-methyl-imazodan; imidazo-quinoxalines; and dihydropyridazinones such as indolidan and LY181512 (5-(6-oxo-1,4,5,6-tetrahydro-pyridazin-3-yl)-1,3-dihydro-indol-2-one); dihydroquinolinone compounds such as cilostamide, cilostazol, and vesnarinone), Type IV phosphodiesterase inhibitors (e.g., quinazolinediones such as nitraquazone and nitraquazone analogs; xanthine derivatives such as denbufylline and arofylline; tetrahydropyrimidones such as atizoram; and oxime carbamates such as filaminast), and Type V phosphodiesterase inhibitors (e.g., sildenafil, zaprinast, dipyridamole, and the compounds described in WO 01/19802 to Aoyama, particularly (S)-2-(2-hydroxymethyl-1-pyrrolidinyl)-4-(3-chloro-4-methoxy-benzylamino)-5-[N-(2-pyrimidinylmethyl)carbamoyl] pyrimidine, 2-(5,6,7,8-tetrahydro-1, 7-naphthyridin-7-yl)-4-(3-chloro-4-methoxybenzylamino)-5-[N-(2-morpholinoethyl)carbamoyl]-pyrimidine, and (S)-2-(2-hydroxymethyl-1-pyrrolidinyl)-4-(3-chloro-4-methoxy-benzylamino)-5-[N-(1,3,5-trimethyl-4-pyrazolyl) carbamoyl]-pyrimidine), and nonspecific phosphodiesterase inhibitors such as theophylline, theobromine, IBMX, pentoxifylline and papaverine.

Other additional active agents that may be co-administered with the antidepressant agent include vasoactive agents such as: nitrates and like compounds such as nitroglycerin, isosorbide dinitrate, erythrityl tetranitrate, amyl nitrate, sodium nitroprusside, molsidomine, linsidomine chlorhydrate ("SIN-1"), S-nitroso-N-acetyl-d,1-penicillamine ("SNAP"), S-nitroso-N-cysteine and S-nitroso-N-glutathione ("SNO-GLU") and diazenium diolates ("NONOates"); long and short acting α-blockers such as phenoxybenzamine, dibenamine, doxazosin, terazosin, phentolamine, tolazoline, prazosin, trimazosin, alfuzosin, tamsulosin and indoramin; ergot alkaloids such as ergotamine and ergotamine analogs, e.g., acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride and terguride; antihypertensive agents such as diazoxide, hydralazine and minoxidil; vasodilators such as nimodepine, pinacidil, cyclandelate, dipyridamole and isoxsuprine; chlorpromazine; haloperidol; yohimbine; Rec15/2739; trazodone; naturally occurring prostaglandins such as $PGE_0$, $PGE_1$, $PGA_1$, $PGB_1$, $PGF_{1\alpha}$, 19-hydroxy-$PGA_1$, 19-hydroxy-$PGB_1$, $PGE_2$, $PGA_2$, $PGB_2$, 19-hydroxy-$PGA_2$, 19-hydroxy-$PGB_2$, $PGE_3$, $PGF_{3\alpha}$; semisynthetic or synthetic derivatives of natural prostaglandins, including carboprost tromethamine, dinoprost tromethamine, dinoprostone, lipoprost, gemeprost, metenoprost, sulprostone and tiaprost; and vasoactive intestinal peptide.

Still other additional active agents that may be co-administered with the non-SRI antidepressant drug include: adrenergic agonists including methoxamine, methpentermine, metaraminol, mitodrine, clonidine, apraclonidine, guanfacine, guanabenz, methyldopa, amphetamine, methamphetamine, epinephrine, norepinephrine, ethylnorepinephrine, phenylephrine, ephedrine, pseudoephedrine, methylphenidate, pemoline, naphazoline, tetrahydrozoline, oxymetazoline, xylometazoline, phenylpropanolamine, phenylethylamine, dopamine, dobutamine, colterol, isoproterenol, isotharine, metaproterenol, terbutaline, metaraminol, tyramine, hydroxyamphetamine, ritodrine, prenalterol, albuterol, isoetharine, pirbuterol, bitolterol, fenoterol, formoterol, procaterol, salmeterol, mephenterine and propylhexedrine; adrenergic antagonists including phenoxybenzamine, phentolamine, tolazoline, prazosin, terazosin, doxazosin, trimazosin, yohimbine, ergot alkaloids, labetalol, ketanserin, urapidil, alifuzosin, bunazosin, tamsulosin, chlorpromazine, haloperidol, phenothiazines, butyrophenones, propranolol, nadolol, timolol, pindolol, metoprolol, atenolol, esmolol, acebutolol, bopindolol, carteolol, oxprenolol, penbutolol, carvedilol, medroxalol, naftopidil, bucindolol, levobunolol, metipranolol, bisoprolol, nebivolol, betaxolol, carteolol, celiprolol, sotalol, propafenone and indoramin; adrenergic neurone blockers including bethanidine, debrisoquine, guabenxan, guanadrel, guanazodine, guanetbidine, guano-clor and guanoxan; benzodiazepines including alprazolam, brotizolam, chlordiazepoxide, clobazepam, clonazepam, clorazepate, demoxepam, diazepam, estazolam, flurazepam, halazepam, lorazepam, midazolam, nitrazepam, nordazapam, oxazepam, prazepam, quazepam, temazepam and triazolam; selective serotonin reuptake inhibitors (using a reduced dose) such as cianopramine, citalopram, femoxetine, fluoxetine, fluvoxamine, ifoxetine, milnacipran, nomifensine, oxaprotiline, paroxetine, sertraline, sibutramine, venlafaxine, viqualine, and zimeldine; and other active agents such as clovoxamine, etoperidone, nefazodone, and opipramol.

Any of the active agents may be administered in the form of a salt, ester, amide, prodrug, active metabolite, conjugate, derivative, or the like, provided that the salt, ester, amide, prodrug, metabolite, conjugate or other derivative is suitable pharmacologically, i.e., effective in the present method. Salts, esters, amides, prodrugs, conjugates and other derivatives of the active agents may be prepared using standard procedures known to those skilled in the art of synthetic organic chemistry and described, for example, by J. March, Advanced Organic Chemistry: Reactions, Mechanisms and Structure, 4th Ed. (New York: Wiley-Interscience, 1992). For example, acid addition salts may be prepared from a free base (e.g., a compound containing a primary amino group) using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of any acidic moieties that may be present may be carried out in a similar manner using a pharmaceutically acceptable base such as sodium hydroxide, potassium hydroxide, ammonium hydroxide, calcium hydroxide, trimethylamine, or the like. Preparation of esters involves reaction of a hydroxyl group with an esterification reagent such as an acid chloride, or esterification of a free carboxylic acid group. Amides may be prepared from esters, using suitable amine reactants, or they may be prepared from an anhydride or an acid chloride by reaction with ammonia or a lower alkyl amine. Prodrugs, conjugates, and active metabolites may also be prepared using techniques known to those skilled in the art or described in the pertinent literature. Prodrugs and conjugates are typically prepared by covalent attachment of a moiety that results in a compound that is therapeutically inactive until modified by an individual's metabolic system.

In addition, many of the active agents contain chiral centers and can thus be in the form of a single isomer or a racemic mixture of isomers. Chiral active agents may be in isomerically pure form, or they may be administered as a racemic mixture of isomers.

Other derivatives and analogs of the active agents may be prepared using standard techniques known to those skilled in the art of synthetic organic chemistry, or may be deduced by reference to the pertinent literature.

III. Pharmaceutical Compositions and Dosage Forms

The compounds of the invention may be administered orally, parenterally, rectally, buccally, sublingually, nasally, by inhalation, topically, transdermally, or via an implanted reservoir in dosage forms containing conventional non-toxic pharmaceutically acceptable carriers and excipients. The term "parenteral" as used herein is intended to include subcutaneous, intravenous, and intramuscular injection. The amount of the compound administered will, of course, be dependent on the particular active agent, the condition or disorder being treated, the severity of the condition or disorder, the subject's weight, the mode of administration and other pertinent factors known to the prescribing physician. Generally, however, dosage will be in the range of approximately 0.001 mg/kg/day to 100 mg/kg/day, more preferably in the range of about 0.1 mg/kg/day to 10 mg/kg/day.

Suitable compositions and dosage forms include tablets, capsules, caplets, gel caps, troches, dispersions, suspensions, solutions, syrups, transdermal patches, gels, powders, magmas, lozenges, creams, pastes, plasters, lotions, discs, suppositories, liquid sprays for nasal or oral administration, dry powder or aerosolized formulations for inhalation, and the like.

Oral dosage forms are preferred for those therapeutic agents that are orally active, and include tablets, capsules, caplets, solutions, suspensions and/or syrups, and may also comprise a plurality of granules, beads, powders or pellets that may or may not be encapsulated. Such dosage forms are prepared using conventional methods known to those in the field of pharmaceutical formulation and described in the pertinent texts, e.g., in Remington: The Science and Practice of Pharmacy, $20^{th}$ Edition, Gennaro, A. R., Ed. (Lippincott, Williams and Wilkins, 2000). Tablets and capsules represent the most convenient oral dosage forms, in which case solid pharmaceutical carriers are employed.

Depending on the intended mode of administration, the pharmaceutical formulation may be a solid, semi-solid or liquid, such as, for example, a tablet, a capsule, caplets, a liquid, a suspension, an emulsion, a suppository, granules, pellets, beads, a powder, or the like, preferably in unit dosage form suitable for single administration of a precise dosage. Suitable pharmaceutical compositions and dosage forms may be prepared using conventional methods known to those in the field of pharmaceutical formulation and described in the pertinent texts and literature, e.g., in Remington: *The Science and Practice of Pharmacy*, 19th Ed. (Easton, PA.: Mack Publishing Co., 1995).

Tablets may be manufactured using standard tablet processing procedures and equipment. Direct compression and granulation techniques are preferred. In addition to the active agent, tablets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the active agent-containing composition may be encapsulated in the form of a liquid or solid (including particulates such as granules, beads, powders or pellets). Suitable capsules may be either hard or soft, and are generally made of gelatin, starch, or a cellulosic material, with gelatin capsules preferred. Two-piece hard gelatin capsules are preferably sealed, such as with gelatin bands or the like. See, for example, *Remington: The Science and Practice of Pharmacy*, Nineteenth Edition. (1995) cited supra, which describes materials and methods for preparing encapsulated pharmaceuticals.

Preferred oral dosage forms are rapid-release formulations, and are therefore effective to provide rapid and systemic absorption of the active agent. Although the time necessary for systemic absorption will depend on the particular dosage form used, it is preferred that the formulation and dosage form provide systemically effective levels of and the desired biological response to the active agent less than 3.5, preferably less than 3, more preferably less than 2.5, still more preferably less than 2.0, and ideally less than 1.5 hours following administration. It is particularly preferred that the formulation and dosage form provide systemically effective levels of the drug and the desired biological response less than 1.0 hour following administration with less than 0.5 hours being most preferred.

Preparations according to this invention for parenteral administration include sterile nonaqueous solutions, suspensions, and emulsions. Examples of nonaqueous solvents or vehicles are propylene glycol, polyethylene glycol, vegetable oils, such as olive oil and corn oil, gelatin, and injectable organic esters such as ethyl oleate. Parenteral formulations may also contain adjuvants such as preserving, wetting, emulsifying, and dispersing agents. The formulations are rendered sterile by incorporation of a sterilizing agent, filtration through a bacteria-retaining filter, irradiation, or heat. They can also be manufactured using a sterile injectable medium.

The active agent may also be administered through the skin or mucosal tissue using conventional transdermal drug delivery systems, wherein the active agent is contained within a laminated structure that serves as a drug delivery device to be affixed to the skin. In such a structure, the drug composition is contained in a layer, or "reservoir," underlying an upper backing layer. The laminated structure may contain a single reservoir, or it may contain multiple reservoirs. In one embodiment, the reservoir comprises a polymeric matrix of a pharmaceutically acceptable contact adhesive material that serves to affix the system to the skin during drug delivery. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. Transdermal drug delivery systems may in addition contain a skin permeation enhancer.

Other modes of administration are suitable as well, with, again, rapid release formulations particularly preferred.

For example, transmucosal administration may be advantageously employed. Transmucosal administration is carried out using any type of formulation or dosage unit suitable for application to mucosal tissue. For example, the selected active agent may be administered to the buccal mucosa in an adhesive tablet or patch, sublingually administered by placing a solid dosage form under the tongue, administered nasally as droplets or a nasal spray, administered by inhalation of an aerosol formulation, a non-aerosol liquid formulation, or a dry powder, placed within or near the rectum ("transrectal" formulations), or administered to the urethra as a suppository, ointment, or the like.

Preferred buccal dosage forms will typically comprise a therapeutically effective amount of the selected active agent and a bioerodible, hydrolyzable, polymeric carrier that may also serve to adhere the dosage form to the buccal mucosa. The buccal dosage unit is fabricated so as to erode fairly quickly, so as to provide for rapid release of the active agent, in turn enabling as-needed administration. The time period is preferably in the range of approximately 0.25 hours to 3.5 hours, preferably about 0.5 to 3 hours, more preferably about 1.0 to 2.5 hours. Buccal drug delivery, as will be appreciated by those skilled in the art, avoids the disadvantages encountered with oral drug administration, e.g., slow absorption, degradation of the active agent by fluids present in the gastrointestinal tract and/or first-pass inactivation in the liver. The dosage unit will generally contain from approximately 1.0 wt. % to about 60 wt. % active agent, preferably on the order of 1 wt. % to about 30 wt. % active agent. With regard to the bioerodible (hydrolyzable) polymeric carrier, it will be appreciated that virtually any such carrier can be used, so long as the desired drug release profile is not compromised, and the carrier is compatible with the active agent to be administered and any other components of the buccal dosage unit. Generally, the polymeric carrier comprises a hydrophilic (water-soluble and water-swellable) polymer that adheres to the wet surface of the buccal mucosa. Examples of polymeric carriers useful herein include acrylic acid polymers and co, e.g., those known as "carbomers" (Carbopol®, which may be obtained from B. F. Goodrich, is one such polymer).

Preferred sublingual dosage forms include sublingual tablets, creams, ointments and pastes. The tablet, cream, ointment or paste for sublingual delivery comprises a therapeutically effective amount of the selected active agent and one or more conventional nontoxic carriers suitable for sublingual drug administration. The sublingual dosage forms of the present invention can be manufactured using conventional processes. The sublingual dosage unit is fabricated to disintegrate rapidly. The time period for complete disintegration of the dosage unit is typically in the range of from about 10 seconds to about 30 minutes, and optimally is less than 5 minutes. In addition to the active agent, other components may also be incorporated into the sublingual dosage forms described herein. The additional components include, but are not limited to binders, disintegrants, wetting agents, lubricants, and the like. Examples of binders that may be used include water, ethanol, polyvinylpyrrolidone, starch solution gelatin solution, and the like. Suitable disintegrants include dry starch, calcium carbonate, polyoxyethylene sorbitan fatty acid esters, sodium lauryl sulfate, stearic monoglyceride, lactose, and the like. Wetting agents, if used, include glycerin, starches, and the like.

In addition to sublingual tablets, other rapidly disintegrating tablets are preferred. Examples of such tablets are well known in the art. Another preferred rapidly disintegrating tablet includes effervescent tablets. Effervescent tablets are described in *Remington*, supra, and examples may be found in the literature, and in, for example, U.S. Pat. No. 5,211,957 to Hagemann et al. Generally, effervescent tablets contain the active agent in combination with additives such as sodium bicarbonate and an organic acid, e.g., tartaric acid or citric acid. In the presence of water, these additives react to liberate carbon dioxide thereby facilitating the disintegration of the tablet. Once the tablet is substantially disintegrated, an individual swallows the resultant solution thereby providing systemic adsorption of the active agent.

Another version of a rapidly disintegrating tablet includes "open matrix network" tablets. These tablets can disintegrate within seconds, i.e., within five to ten seconds, after being placed on the tongue of an individual. The contents of the tablet can then be swallowed with or without water. An example of such a tablet is found in U.S. Pat. No. 4,371,516 to Gregory et al. As described therein, the carrier provides a low-density network, e.g., about 10 to about 200 mg/cm$^3$, of water-soluble or water-dispersible material. The tablet is produced by subliming a solution containing both the drug and carrier that is subsequently directed to a mold having tablet-shaped depressions. The carrier may be any suitable material, but is preferably gelatin, with partially hydrolyzed gelatin most preferred.

Another example of a rapidly disintegrating tablet is described in U.S. Pat. No. 5,466,464 to Masaki et al. As described therein, an agar solution is prepared using conventional techniques, such as adding agar powder to water followed by gentle heating. Lactose and/or mannitol along with the active agent are added to the agar solution and mixed until uniform. Excipients, e.g., sweeteners, preservatives, and so forth, are also added. Thereafter, aliquots of the mixture are placed in individual molds corresponding to the desired shape of the dosage form. Upon cooling, the mixture solidifies into a "jelly form," which is then dried using conventional techniques, e.g., by reducing the pressure to vacuum-like conditions or aerating, thereby forming a rapidly disintegrating tablet. These and other rapidly disintegrating tablets are available using technology available from Yamanouchi Pharma Technologies, Inc. (Palo Alto, Calif.), some dosage forms of which are marketed under the WOWTAB® trademark.

In addition to sublingual tablets, other rapidly disintegrating tablets may also be used. For example, other suitable rapidly disintegrating tablets are effervescent tablets. Effervescent tablets are described in *Remington*, supra, and examples may be found in the literature, and in, for example, U.S. Pat. No. 5,211,957 to Hagemann et al. Generally, effervescent tablets contain the active agent in combination with additives such as sodium bicarbonate and an organic acid, e.g., tartaric acid or citric acid. In the presence of water, these additives react to liberate carbon dioxide thereby facilitating the disintegration of the tablet. Once the tablet is substantially disintegrated, an individual swallows the resultant solution thereby providing systemic adsorption of the active agent.

Another version of a rapidly disintegrating tablet is an "open matrix network" tablet. These tablets can disintegrate within seconds, i.e., within five to ten seconds, after being placed on the tongue. The contents of the tablet can then be swallowed with or without water. One such tablet is described in U.S. Pat. No. 4,371,516 to Gregory et al. As indicated therein, the carrier provides a low-density network, e.g., about 10 to about 200 mg/cm$^3$, of a water-soluble or water-dispersible material. The tablet is produced by subliming a solution containing both the drug and carrier that is subsequently directed to a mold having tablet-shaped depressions. The carrier may be any suitable material, but is preferably gelatin, with partially hydrolyzed gelatin most preferred.

Another example of a rapidly disintegrating tablet is described in U.S. Pat. No. 5,466,464 to Masaki et al., which describes preparation of an agar solution using conventional techniques, such as adding agar powder to water followed by gentle heating. Lactose and/or mannitol along with the active agent are added to the agar solution and mixed until uniform. Excipients, e.g., sweeteners, preservatives, and so forth, are also added. Thereafter, aliquots of the mixture are placed in individual molds corresponding to the desired shape of the dosage form. Upon cooling, the mixture solidifies into a "jelly form," which is then dried using conventional techniques, e.g., by reducing the pressure to vacuum-like conditions or aerating, thereby forming a rapidly disintegrating tablet. These and other rapidly disintegrating tablets are available using technology available from Yamanouchi Pharma Technologies, Inc. (Palo Alto, Calif.), some dosage forms of which are marketed under the WOWTAB® name.

In addition, the active agent may be administered via a chewing gum formulation. Gum formulations containing a pharmacologically active agent and techniques for preparing such formulations are well known in the art. For example, a gum base (available commercially from, for example, Cafosa, Inc., Calabria, Spain) is rolled in a suitable roller at about 10 to 85° C. for about three minutes. Thereafter, all components except for the active agent, e.g., plasticizers, sugars, sweeteners, fillers, polymers and waxes, are added sequentially and rolled until a homogenous material is obtained. Then, active agent is added and rolled until the entire material is homogenous. Once homogenous, the material is removed from the roll, cooled to room temperature and processed into the desired gum shape, e.g., cubes or sticks.

For transurethral administration, the formulation comprises a urethral dosage form containing the active agent and one or more selected carriers or excipients, such as water, silicone, waxes, petroleum jelly, polyethylene glycol ("PEG"), propylene glycol ("PG"), liposomes, sugars such as mannitol and lactose, and/or a variety of other materials, with polyethylene glycol and derivatives thereof particularly preferred. Transurethral drug administration, as explained in U.S. Pat. Nos. 5,242,391, 5,474,535, 5,686,093 and 5,773,020 to Place et al., can be carried out in a number of different ways using a variety of urethral dosage forms. For example, the drug can be introduced into the urethra from a flexible tube, squeeze bottle, pump or aerosol spray. The drug may also be contained in coatings, pellets or suppositories that are absorbed, melted or bioeroded in the urethra. In certain embodiments, the drug is included in a coating on the exterior surface of a penile insert. A preferred drug delivery device for administering a drug transurethrally is described and illustrated in the aforementioned U.S. patents to Place et al.

Preferred transrectal dosage forms include rectal suppositories, creams, ointments, and liquid formulations (enemas). The suppository, cream, ointment or liquid formulation for transrectal delivery comprises a therapeutically effective amount of the selected active agent and one or more conventional nontoxic carriers suitable for transrectal drug administration. The transrectal dosage forms of the present invention can be manufactured using conventional processes. The transrectal dosage unit can be fabricated to disintegrate rapidly or over a period of several hours. The time period for complete disintegration is preferably in the range of from about 10 minutes to about 6 hours, and optimally is less than 3 hours.

The active agents may also be administered intranasally or by inhalation. Compositions for nasal administration are generally liquid formulations for administration as a spray or in the form of drops, although powder formulations for intranasal administration, e.g., insufflations, are also known. Formulations for inhalation may be prepared as an aerosol, either a solution aerosol in which the active agent is solubilized in a carrier (e.g., propellant) or a dispersion aerosol in which the active agent is suspended or dispersed throughout a carrier and an optional solvent. Non-aerosol formulations for inhalation may take the form of a liquid, typically an aqueous suspension, although aqueous solutions may be used as well. In such a case, the carrier is typically a sodium chloride solution having a concentration such that the formulation is isotonic relative to normal body fluid. In addition to the carrier, the liquid formulations may contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitan monopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Non-aerosol formulations for inhalation may also comprise dry powder formulations, particularly insufflations in which the powder has an average particle size of about 0.1 $\mu$m to 50 $\mu$m, preferably 1 $\mu$m to about 25 $\mu$m.

IV. Dosage and Administration

The present formulations are administered on an as-needed basis, as explained previously. Such flexibility in administration is desirable since the individual may administer the formulation at any convenient time within a 0.25-hour to 3-hour window prior to anticipated sexual activity. In addition, because they are all systemically acting, the formulations may be discreetly administered without need for a device.

As stated above, the amount of active agent administered, and the dosing regimen used, will, of course, be dependent on, inter alia, the age and general condition of the individual being treated, the degree to which the onset of ejaculation is to be delayed, and the judgment of the prescribing physician. The concentration of active agent in any given dosage form can vary a great deal, and will depend on a variety of factors, including the type of composition or dosage form, the corresponding mode of administration, the nature and activity of the specific active agent, and the intended drug release profile.

As will appreciated by those skilled in the art, the methods and dosage forms of the invention relate to systemic administration. In order to achieve systemically effective levels of a drug, a typical as-needed dose of the active agent is generally in the range of from about 0.1 mg to about 300 mg, preferably of from about 1 mg to about 200 mg with a dose in the range of from about 1 mg to about 50 mg being most preferred. Thus, unit dosage forms preferably contain the active agent in these ranges as well, i.e., from about 0.1 mg to about 300 mg, more preferably from about 1 mg to about 200 mg with about 1 mg to about 50 mg of active agent in each unit dose form. The dosing regimen can be modulated in order to achieve satisfactory control of the onset of ejaculation. These amounts are particularly preferred when the active agent is clomipramine or clomipramine hydrochloride.

V. Packaged Kits

In another embodiment, a packaged kit is provided that contains the pharmaceutical formulation to be administered, i.e., a pharmaceutical formulation containing a non-SRI antidepressant drug for the treatment of premature ejaculation, a container, preferably sealed, for housing the formulation during storage and prior to use, and instructions for carrying out drug administration in a manner effective to treat premature ejaculation. The instructions will typically be written instructions on a package insert and/or on a label. Depending on the type of formulation and the intended mode of administration, the kit may also include a device for administering the formulation (e.g., a transurethral drug delivery device such as shown in FIG. 1). The formulation may be any suitable formulation as described herein. For example, the formulation may be an oral dosage form containing a unit dosage of the active agent. The kit may contain multiple formulations of different dosages of the same agent. The kit may also contain multiple formulations of different active agents.

It is to be understood that while the invention has been described in conjunction with the preferred specific embodiments thereof, the foregoing description is intended to illustrate and not limit the scope of the invention. Other aspects, advantages and modifications will be apparent to those skilled in the art to which the invention pertains. Furthermore, the practice of the present invention will employ, unless otherwise indicated, conventional techniques of drug formulation that are within the skill of the art. Such techniques are fully explained in the literature. See *Remington: The Science and Practice of Pharmacy*, cited supra, as well as Goodman & Gilman's *The Pharmacological Basis of Therapeutics,* 9th Ed. (New York: McGraw-Hill, 1996).

All patents, patent applications, patent publications, journal articles and other references cited herein are incorporated by reference in their entireties.

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

EXAMPLE 1

An effervescent tablet is prepared containing the following components:

| Component | Amount (per tablet) |
| --- | --- |
| Clomipramine hydrochloride | 300 mg |
| Sodium bicarbonate | 1985 mg |
| Citric acid | 1000 mg |

The components (i.e., clomipramine hydrochloride, sodium bicarbonate and citric acid, as set forth in the above table) are thoroughly mixed. An effervescent tablet is produced by placing the mixture in a die followed by compression with an appropriate punch. Relatively little compression force is used, e.g., about 3,000 to about 20,000 pounds of force.

EXAMPLE 2

A buccal tablet is prepared containing the following components:

| Component | Amount (per tablet) |
| --- | --- |
| Clomipramine hydrochloride | 10 mg |
| Gelatin | 90 mg |
| Glycerin (concentrated) | 20 mg |
| Lactose | 10 mg |
| Mannitol | 20 mg |

Clomipramine hydrochloride (10 g) and 90 g of gelatin are mixed and pulverized in a mill. After the mixing is complete, 20 g of concentrated glycerin, 10 g of lactose and 20 g of mannitol are added and the components are mixed until uniform. 150 mg aliquot portions of the mixture are compression-molded to provide a buccal dosage unit. Each buccal unit contains 10 mg of clomipramine hydrochloride.

EXAMPLE 3

A sublingual tablet is prepared containing the following components:

| Component | Amount (% by weight) |
| --- | --- |
| Clomipramine hydrochloride | 35% |
| Lactose | 63.67% |
| Polyethylene glycol 3350 | 1.0% |
| Magnesium stearate | 0.33% |

The components (i.e., clomipramine hydrochloride, lactose, polyethylene glycol 3350 and magnesium stearate, as set forth in the above table) are thoroughly mixed. A sublingual tablet is produced by placing the mixture in a die followed by compression with an appropriate punch. Relatively little compression force is used, e.g., about 3,000 to about 20,000 pounds of force.

EXAMPLE 4

An "open matrix network" tablet is prepared. A solution containing the following components is prepared:

| Component | Amount |
| --- | --- |
| Clomipramine hydrochloride | 50 g |
| Partially hydrolyzed gelatin | q.s. to 1,000 ml |

A metal mold containing cylindrical depressions (each depression is about 0.5 cm in diameter and about 1.0 cm deep) is cooled to about −192° C. with liquid nitrogen. The clomipramine is mixed with the partially hydrolyzed gelatin solution. With continuous mixing, 0.5 ml of the solution is transferred into each depression. After the solution freezes, the mold is placed in a vacuum chamber at room temperature under a vacuum of 0.3 mm Hg for 12 hours. The dosage forms, each containing about 25 mg of the active agent, are then removed from the molds. The dosage forms disintegrate rapidly, i.e., from about five to ten seconds when administered orally.

EXAMPLE 5

A solution for use in a sublingual spray or pulmonary inhaler is prepared. The solution is prepared according to the following:

| Component | Amount |
| --- | --- |
| Clomipramine hydrochloride | 2.5 g |
| Benzalkonium chloride | 0.100 g |
| Distilled water | q.s. to 100 ml |

The formulation is prepared by initially forming a clomipramine hydrochloride solution by combining, under aseptic conditions, 2.5 g of clomipramine hydrochloride in 50 ml of distilled water. Sodium chloride may be added such that the final solution is isotonic. The amount of sodium chloride necessary to provide a final isotonic solution can be calculated based on equations provided in the literature or can be determined experimentally by those skilled in the art. Benzalkonium chloride is used as a preservative and is added to the solution followed by mixing.

The solution is then placed into a spray bottle, which typically comprises a collapsible container vessel, an applicator and a cap. For sublingual sprays, the applicator is shaped and sized to be received under the tongue. For pulmonary administration, the applicator is shaped and sized to facilitate tracheal inhalation by an individual. The applicator will have an opening to release a spray or mist of the solution.

The spray bottle is designed to deliver an individual dose with one to three compressions of the bottle to deliver an effective dose. For example, a single compression of the bottle may be designed to administer approximately 0.33 ml of liquid as a mist or spray. In the context of the formulation described above housed in such a bottle, one or more compressions of the bottle will provide an effective dose of clomipramine.

EXAMPLE 6

A gum formulation is prepared. The components of the gum formulation are as follows:

| Component | Amount (% by weight) |
|---|---|
| Clomipramine hydrochloride | 2% to 30% |
| Gum base (Cafosa TAB-3-T, available from Cafosa, Inc., Calabria, Spain) | 15% to 50% |
| Sorbitol powder | 10% to 50% |

Cafosa gum base TAB-3-T is rolled in a suitable roller at about 45° C. for about three minutes. Thereafter, the sorbitol powder is added and rolled for about four minutes to obtain a homogenous mixture. Clomipramine hydrochloride is then added to and rolled with the material for another three minutes. The rolled material is removed from the rolling equipment, cooled to room temperature and processed into the small cubes. Each cube contains a therapeutically effective amount of the active agent.

EXAMPLE 7

A rapidly disintegrating tablet is prepared. The general formulation is as follows:

| Component | Amount (approximately) | Preferred Amount (approximately) |
|---|---|---|
| Active agent (e.g., clomipramine hydrochloride) | 0.001 to 50 parts | 0.01 to 20 parts |
| Lactose and/or mannitol | 50 to 99.999 parts | 80 to 99.9 parts |
| Agar and excipients (e.g., sweetener, coloring agent, preservative, etc.) | 0.12 to 1.2 parts | 0.2 to 0.4 parts |

An aqueous solution containing 0.3 to 2.0%, preferably 0.3 to 0.8%, of agar is prepared and the above components are added to the solution and mixed to obtain a suspension. The suspension is then filled in a suitable mold at room temperature and then dried. Suitable drying procedures include exposing the suspension for two to five hours at reduced pressure, e.g., at or near vacuum conditions, at a temperature of from about 25° C. to about 35° C. In addition, the suspension may be dried via aeration drying at a temperature of from about 3° C. to about 15° C. for one to six days. The tablets may have a size of about 9.5 mm in diameter and about 4.2 mm thick or about 12 mm in diameter and about 5.2 mm thick.

EXAMPLE 8

A rapidly disintegrating tablet for as-needed administration of clomipramine hydrochloride to treat premature ejaculation was prepared. The tablet contains a 10 mg unit dosage of clomipramine, with the remainder of the tablet containing the following components:

| COMPONENT | % SOLID (W/W) | QUANTITY PER TABLET (MG) | QUANTITY PER BATCH (G) |
|---|---|---|---|
| Clomipramine HCl | 8.333 | 10.00 | 100.00 |
| Mannitol | 84.417 | 101.30 | 1013.00 |
| Maltose | 5.000 | 6.00 | 60.00 |
| Acesulfame Potassium | 0.500 | 0.60 | 6.00 |
| Peppermint (Beta Natural) | 0.250 | 0.30 | 3.00 |
| Magnesium Stearate | 0.750 | 9.00 | 9.00 |
| Stearic Acid (Micronized) | 0.750 | 9.00 | 9.00 |
| Purified Water* | — | — | — |
| Total | 100.000 | 120.00 | 1200.0 |

*Purified water is removed during processing and is not part of the final formula.

EXAMPLE 9

The patients for the study are drawn from a waiting list for psychosexual therapy of a sexology outpatient department and through advertisement. The inclusion criteria are that the patients be heterosexual, be aged 18–75 years, be involved in a sexual relationship with a female partner during the previous 6 months, the partner is able to participate in the study, and the patient experiences premature ejaculation.

Patients are excluded if they used psychoactive medication, are receiving any therapy for sexual dysfunction, have inhibited male orgasm, are alcohol or substance abusers, score greater than 14 on the 24-item Hamilton Rating Scale for Depression (HAM-D) indicating clinically significant depression, and for other clinically significant medical disease or symptomology. For the duration of the study, the patients are required to abstain from alcohol.

Patients are randomly assigned to double blind treatment with any rapid-release formulation described in the previous examples or a placebo. Patients who remain in the study for at least 3 weeks are included in the statistical analysis. Patients are provided with formulations prepared in the preceding Examples for administration or matching placebo. Patients are instructed to administer the formulation at any time within the four-hour window leading up to anticipated sexual activity. During the study, the patients do not use condoms or topical anesthetics.

Patients and their partners are assessed at the end of each week. Efficacy measures include (1) frequency of attempted intercourse, (2) latency to attempted ejaculation (from penetration), (3) frequency of successful attempts at intercourse without premature ejaculation, (4) number of incidences of premature ejaculation, and (5) time to ejaculation as reported by both the patients and their partners based on subjective measurements. In addition, the patients are assessed using the following psychopathological rating instruments: Hamilton Depression Rating Scale (HDRS), Clinical Global Impression (CGI), COVI Anxiety Scale, Atypical Depressive Disorders Scale-Changes (ADDS-C) and an adverse event form.

The response to treatment is scored. The mean or median values are analyzed by using parametric tests including Friedman two-way analysis of variance (ANOVA) and the Wilcoxon matched-pairs signed-ranks test to assess differences in measurements within the groups, and the Mann-Whitney test for differences between the groups. Differences between groups on discrete variables are tested for statistical significance by using Fisher's exact test. A two-tailed p value 0.05 is considered significant for these analyses.

Each of the formulations prepared and administered for systemic absorption is expected to be effective in treating premature ejaculation. The use of the formulations results in an extension of intravaginal ejaculation latency time in patients with premature ejaculation. The data from patient-rated and partner-rated latency to ejaculation is compared. Both of these parameters show greater improvement with clomipramine-containing formulations as compared to placebo. In addition, those patients who attempted to treat their premature ejaculation with previous modalities report greater satisfaction with on demand administration of the formulations provided in the examples. Specifically, these patients cited greater flexibility with the timing of the dose, and fewer side effects (in part due to not administering clomipramine on a daily basis).

We claim:

1. A method for treating premature ejaculation, which comprises systemically administering to a male individual in need of such treatment, less than 3.5 hours prior to anticipated sexual activity, a rapid-release pharmaceutical formulation containing a therapeutically effective amount of an antidepressant drug selected from the group consisting of tricyclic antidepressants, tetracyclic antidepressants, monoamine oxidase inhibitors, azaspirone antidepressants, and atypical non-SRI antidepressants, wherein the formulation releases the drug at a rate that provides a systemically effective level of the drug within 3.5 hours of adminstration.

2. The method of claim 1, wherein the antidepressant drug is contained within a pharmaceutical formulation.

3. The method of claim 2, wherein the pharmaceutical formulation is a unit dosage form.

4. The method of claim 2, wherein the antidepressant drug is administered immediately prior to anticipated sexual activity.

5. The method of claim 1, wherein the antidepressant drug is administered about 0.25 to about 3.5 hours prior to anticipated sexual activity.

6. The method of claim 5, wherein the antidepressant drug is administered about 0.5 to about 3.0 hours prior to anticipated sexual activity.

7. The method of claim 6, wherein the antidepressant drug is administered about 1 to about 2.5 hours prior to anticipated sexual activity.

8. The method of any one of claims 4, 5, 6 and 7, wherein the sexual activity is sexual intercourse.

9. The method of claim 2, wherein the formulation is a rapid-release dosage form.

10. The method of claim 3, wherein the formulation is a rapid-release unit dosage form.

11. The method of claim 2, wherein the pharmaceutical formulation is administered orally.

12. The method of claim 11, wherein the pharmaceutical formulation is selected from the group consisting of tablets, capsules, caplets, solutions, suspensions syrups granules, beads, powders and pellets.

13. The method of claim 12, wherein the pharmaceutical formulation comprises a tablet.

14. The method of claim 12, wherein the pharmaceutical formulation comprises a capsule.

15. The method of claim 1, wherein the antidepressant drug is administered transmucosally.

16. The method of claim 15, wherein the antidepressant drug is administered sublingually.

17. The method of claim 15, wherein the antidepressant drug is administered buccally.

18. The method of claim 15, wherein the antidepressant drug is administered intranasally.

19. The method of claim 15, wherein the antidepressant drug is administered transurethrally.

20. The method of claim 15, wherein the antidepressant drug is administered rectally.

21. The method of claim 1, wherein the antidepressant drug is administered by inhalation.

22. The method of claim 1, wherein the antidepressant drug is administered transdermally.

23. The method of claim 1, wherein the active agent is administered parenterally.

24. The method of claim 1, wherein the antidepressant drug is selected from the group consisting of tricyclic antidepressants, tetracyclic antidepressant drugs, and combinations thereof.

25. The method of claim 24, wherein the antidepressant drug is selected from the group consisting of amitryptiline, amoxapine, butriptyline, demexiptiline, desipramine, dibenzepin, dimetacrine, dothiepin, doxepin, imipramine, iprindole, lofepramine, maprotiline, melitracen, metapramine, mianserin, mirtazapine, nortryptiline, propizepine, protriptyline, quinupramine, setiptiline, tianeptine, trimipramine, and combinations thereof.

26. The method of claim 1, wherein the antidepressant drug is a monoamine oxidase inhibitor.

27. The method of claim 26, wherein the monoamine oxidase inhibitor is selected from the group consisting of amiflamine, brofaromine, clorgyline, α-ethyltryptamine, iproclozide, iproniazid, isocarboxazid, mebanazine, moclobemide, nialamide, pargyline, phenelzine, pheniprazine, pirlindole, safrazine, selegiline, toloxatone, tranylcypromine, and combinations thereof.

28. The method of claim 1, wherein the antidepressant drug is an azaspirone antidepressant.

29. The method of claim 28, wherein the azaspirone antidepressant is selected from the group consisting of buspirone, gepirone, ipsapirone, tandospirone, tiaspirone, and combinations thereof.

30. The method of claim 1, wherein the antidepressant drug is an atypical non-SRI antidepressant selected from the group consisting of amesergide, amineptine, benactyzine, bupropion, fezolamine, levoprotiline, medifoxamine, mianserin, minaprine, oxaflozane, oxitriptan, rolipram, teniloxazine, tofenacin, trazodone, tryptophan, viloxazine, and combinations thereof.

31. The method of claim 1, further comprising administering at least one additional active agent with the antidepressant drug.

32. The method of claim 31, wherein the additional active agent is a vasoactive agent selected from the group consisting of nitroglycerin, isosorbide dinitrate, erythrityl tetranitrate, amyl nitrate, sodium nitroprusside, molsidomine, linsidomine chlorhydrate, S-nitroso-N-acetyl-d,l-penicillamine, S-nitroso-N-cysteine and S-nitroso-N-glutathione, diazenium diolates ("NONOates"), phenoxybenzamine, dibenamine, doxazosin, terazosin, phentolamine, tolazoline, prazosin, trimazosin, alfuzosin, tamsulosin, indoramin, ergotamine, acetergamine, brazergoline, bromerguride, cianergoline, delorgotrile, disulergine, ergonovine maleate, ergotamine tartrate, etisulergine, lergotrile, lysergide, mesulergine, metergoline, metergotamine, nicergoline, pergolide, propisergide, proterguride, diazoxide, hydralazine, minoxidil nimodepine, pinacidil, cyclandelate, dipyridamole, isoxsuprine, chlorpromazine, haloperidol, yohimbine, prostaglandin $E_0$, prostaglandin $E_1$, prostaglandin $A_1$, prostaglandin $B_1$, prostaglandin $F_{1\alpha}$, 19-hydroxy-prostaglandin $A_1$, 19-hydroxy-prostaglandin $B_1$, prostaglandin $E_2$, prostaglandin $A_2$, prostaglandin $B_2$, 19-hydroxy-prostaglandin $A_2$, 19-hydroxy-prostaglandin $B_2$, prostaglandin $E_3$, prostaglandin $F_{3\alpha}$, carboprost tromethamine, dinoprost tromethamine, dinoprostone, lipoprost, gemeprost, metenoprost, sulprostone, tiaprost, vasoactive intestinal peptide, and combinations thereof.

33. The method of claim 31, wherein the additional active agent is a phosphodiesterase inhibitor.

34. The method of claim 34, wherein the phosphodiesterase inhibitor is a Type III, Type IV, Type V, or nonspecific phosphodiesterase inhibitor.

35. The method of claim 31, wherein the additional active agent is selected form the group consisting of cianopramine, citalopram, femoxetine, fluoxetine, fluvoxamine, ifoxetine, milnacipran, nomifensine, oxaprotiline, paroxetine, sertraline, sibutramine, venlafaxine, viqualine, zimeldine, clovoxamine, etoperidone, methylphenidate, nefazodone, opipramol, 2-methyl serotonin, lysergic acid diethylamide, ergot alkaloids, 8-hydroxy-(2-N,N-dipropylamino)-tetraline, 1-(4-bromo-2,5-dimethoxyphenyl)-2-aminopropane, cisapride, sumatriptan, m-chlorophenylpiperazine, zacopride, mezacopride, ondansetron, granisetron, metoclopramide, tropisetron, dolasetron, trimethobenzamide, methysergide, risperidone, ketanserin, ritanserin, clozapine, R(+)--(2,3-dimethoxyphenyl)-1-[2-(4-fluorophenyl)ethyl]-4-piperidine-methanol, azatadine, cyproheptadine, fenclonine, dexfenfluramine, fenfluramine, chlorpromazine, methoxamine, methpentermine, metaraminol, mitodrine, clonidine, apraclonidine, guanfacine, guanabenz, methyldopa, amphetamine, methamphetamine, epinephrine, norepinephrine, ethylnorepinephrine, phenylephrine, ephedrine, pseudoephedrine, pemoline, naphazoline, tetrahydrozoline, oxymetazoline, xylometazoline, phenylpropanolamine, phenylethylamine, dopamine, dobutamine, colterol, isoproterenol, isotharine, metaproterenol, terbutaline, tyrarnine, hydroxyamphetamine, ritodrine, prenalterol, albuterol, isoetharine, pirbuterol, bitolterol, fenoterol, formoterol, procaterol, salmeterol, mephenterine, propylhexedrine, phenoxybenzamine, phentolamine, tolazoline, prazosin, terazosin, doxazosin, trimazosin, yohimbine, labetalol, urapidil, alfuzosin, bunazosin, tamsulosin, haloperidol, phenothiazines, butyrophenones, propranolol, nadolol, timolol, pindolol, metoprolol, atenolol, esmolol, acebutolol, bopindolol, carteolol, oxprenolol, penbutolol, carvedilol, medroxalol, naftopidil, bucindolol, levobunolol, metipranolol, bisoprolol, nebivolol, betaxolol, carteolol, celiprolol, sotalol, propafenone, indoramin, bethanidine, debrisoquine, guabenxan, guanadrel, guanazodine, guanethidine, guanoclor, guanoxan, alprazolam, brotizolam, chlordiazepoxide, clobazepam, clonazepam, clorazepate, demoxepam, diazepam, estazolam, flurazepam, halazepam, lorazepam, midazolam, nitrazepam, nordazapam, oxazepam, prazepam, quazepam, temazepam, triazolam, pharmacologically acceptable salts thereof, and combinations of any of the foregoing.

36. The method of claim 35, wherein the additional active agent is selected from the group consisting of alprazolam, brotizolam, chlordiazepoxide, clobazepam, clonazepam, clorazepate, demoxepam, diazepam, estazolam, flurazepam, halazepam, lorazepam, midazolam, nitrazepam, nordazapam, oxazepam, prazepam, quazepam, temazepam, triazolam, and pharmaceutically acceptable salts thereof.

37. The method of claim 35, wherein the additional active agent is selected from the group consisting of fluoxetine, fluvoxamine, paroxetine, sertraline, and pharmaceutically acceptable salts thereof.

38. A pharmaceutical formulation for treating premature ejaculation, comprising a rapid-release formulation of a therapeutically effective amount of an antidepressant drug selected from the group consisting of tricyclic antidepressants, tetracyclic antidepressants, MAO inhibitors, azaspirone antidepressants, and atypical non-SRI antidepressants, in an amount to delay the onset of ejaculation by the individual during sexual activity, and a pharmaceutically acceptable carrier, wherein the formulation releases the drug at a rate effective to provide a systemically effective level of the drug within 3.5 hours of adminstration to a patient.

39. The formulation of claim 38, wherein the antidepressant drug is selected from the group consisting of tricyclic antidepressants, tetracyclic antidepressant drugs, and combinations thereof.

40. The formulation of claim 39, wherein the antidepressant drug is selected from the group consisting of amitryptiline, amoxapine, butriptyline, demexiptiline, desipramine, dibenzepin, dimetacrine, dothiepin, doxepin, imipramine, iprindole, lofepramine, maprotiline, melitracen, metapramine, mianserin, mirtazapine, nortryptiline, propizepine, protriptyline, quinupramine, setiptiline, tianeptine, trimipramine, and combinations thereof.

41. The formulation of claim 38, wherein the antidepressant drug is selected from the group consisting of monoamine oxidase inhibitors.

42. The formulation of claim 41, wherein the antidepressant drug is selected from the group consisting of amiflamine, brofaromine, clorgyline, α-ethyltryptamine, iproclozide, iproniazid, isocarboxazid, mebanazine, moclobemide, nialamide, pargyline, phenelzine, pheniprazine, pirlindole, safrazine, selegiline, toloxatone, tranylcyprornine, and combinations thereof.

43. The formulation of claim 38, wherein the antidepressant drug is selected from the group consisting of azaspirone antidepressants.

44. The formulation of claim 43, wherein the antidepressant drug is selected from the group consisting of buspirone, gepirone, ipsapirone, tandospirone, tiaspirone, and combinations thereof.

45. The formulation of claim 38, wherein the antidepressant drug is an atypical non-SRI antidepressant selected from the group consisting of amesergide, amineptine, benactyzine, bupropion, fezolamine, levoprotiline, medifoxamine, mianserin, minaprine, oxaflozane, oxitriptan, rolipram, teniloxazine, tofenacin, trazodone, tryptophan, viloxazine, and combinations thereof.

46. The formulation of claim 38, in unit dosage form.

47. The formulation of claim 46, wherein the antidepressant drug is present in an amount of about 0.1 mg to about to about 300 mg.

48. The formulation of claim 47, wherein the amount is in the range of about 1 mg to about 100 mg.

49. The formulation of claim 48, wherein the amount is in the range of about 1 mg to about 50 mg.

50. The formulation of claim 38, in the form of a rapidly disintegrating tablet.

51. The formulation of claim 38, in the form of an effervescent tablet.

52. The formulation of claim 38, in the form of an open matrix network tablet.

53. A formulation of claim 38, adapted for transmucosal drug administration, wherein the carrier is suitable for transmucosal drug delivery buccally, sublingually, intranasally, rectally, or by inhalation.

54. The formulation of claim 53, comprising a solid dosage form for application to the buccal mucosa, and wherein the carrier is suitable for buccal drug delivery.

55. The formulation of claim 54, wherein the carrier is a hydrolyzable polymer.

56. The formulation of claim 55, wherein the dosage form further comprises an adhesive suitable for affixing the dosage form to the buccal mucosa.

57. The formulation of claim 53, comprising a dosage form for application to the sublingual mucosa, and wherein the carrier is suitable for sublingual drug delivery.

58. The formulation of claim 53, comprising a dosage form for application to the rectal mucosa, and the carrier is suitable for rectal drug delivery.

59. The formulation of claim 58, comprising a rectal suppository.

60. The formulation of claim 53, comprising a dosage form suitable for inhalation.

61. The formulation of claim 60, comprising a liquid.

62. The formulation of claim 60, comprising a dry powder.

63. The formulation of claim 60, comprising an aerosol composition.

64. The pharmaceutical formulation of claim 38, comprising an intranasal solution.

65. The formulation of claim 38, in the form of a gum.

66. The formulation of claim 38, in the form of a transdermal drug delivery device adapted to be affixed to an individual's body surface.

67. A packaged kit for a patient to use in the treatment of premature ejaculation, comprising: a rapid-release pharmaceutical formulation of an antidepressant drug selected from the group consisting of tricyclic antidepressants, tetracyclic antidepressants, MAO inhibitors, azaspirone antidepressants, and atypical non-SRI antidepressants, wherein the formulation releases the drug at a rate effective to provide a systemically effective level of the drug within 3.5 hours of adminstration to a patient; a container housing the pharmaceutical formulation during storage and prior to administration; and instructions for carrying out drug administration in a manner effective to treat premature ejaculation.

68. The packaged kit of claim 67, wherein the pharmaceutical formulation is a rapid-release dosage form containing a unit dosage of the antidepressant drug, the unit dosage being a therapeutically effective dosage for treatment of premature ejaculation.

* * * * *